United States Patent
Leussler et al.

(10) Patent No.: US 10,918,283 B2
(45) Date of Patent: Feb. 16, 2021

(54) REAL TIME ENERGY DEPOSITING THERAPY SYSTEM CONTROLLED BY MAGNETIC RESONANCE RHEOLOGY

(71) Applicant: KONINKLIJKE PHILIPS N.V., Eindhoven (NL)

(72) Inventors: Christoph Leussler, Eindhoven (NL); Daniel Wirtz, Eindhoven (NL); Peter Vernickel, Eindhoven (NL); Peter Mazurkewitz, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1411 days.

(21) Appl. No.: 14/781,717

(22) PCT Filed: Mar. 28, 2014

(86) PCT No.: PCT/EP2014/056288
§ 371 (c)(1),
(2) Date: Oct. 1, 2015

(87) PCT Pub. No.: WO2014/161783
PCT Pub. Date: Oct. 9, 2014

(65) Prior Publication Data
US 2016/0038081 A1 Feb. 11, 2016

(30) Foreign Application Priority Data
Apr. 5, 2013 (EP) .................................... 13162495

(51) Int. Cl.
*A61B 5/00* (2006.01)
*A61B 18/18* (2006.01)
(Continued)

(52) U.S. Cl.
CPC ............ *A61B 5/0036* (2018.08); *A61B 5/055* (2013.01); *A61B 5/4836* (2013.01);
(Continued)

(58) Field of Classification Search
CPC ....... A61B 5/4836; A61B 5/055; A61B 90/37; A61B 18/1815; A61N 7/02; G01R 33/4808
See application file for complete search history.

(56) References Cited

U.S. PATENT DOCUMENTS 4,628,737 A * 12/1986 Charles ............... E02B 17/0034
73/624
5,164,920 A * 11/1992 Bast ...................... B06B 1/0622
310/322
(Continued)

FOREIGN PATENT DOCUMENTS

| JP | 0852152 A | 2/1996 |
|---|---|---|
| WO | 03075771 A1 | 9/2003 |
| WO | 2013030746 A1 | 3/2013 |

OTHER PUBLICATIONS

Muthipillai et al., "Magnetic Resonance Imaging of Acoustic Strain Waves" Proc. Soc. Magn. Reson. 1, p. 189 (1995).
(Continued)

*Primary Examiner* — Joanne M Hoffman
(74) *Attorney, Agent, or Firm* — Sherry Austin

(57) ABSTRACT

An energy depositing therapy system (10), comprising:
an energy depositing unit (12) provided for locally depositing energy into a therapy zone (56) of a subject of interest (28) for therapy purposes;
a transducer unit (32) that is provided for applying mechanical oscillations to at least a portion of the subject of interest (28);
a magnetic resonance imaging system (14) provided for acquiring magnetic resonance imaging data from at least the portion of a subject of interest (28), comprising an image processing unit (24) configured to image the mechanical oscillations;
a control unit (40) that is connectable to the energy depositing unit (12), the transducer unit (32) and a
(Continued)

magnetic resonance scanner (16) of the magnetic resonance imaging system (14), wherein
the control unit (40) is configured to control the depositing of energy in dependence of the processed magnetic resonance imaging data of the portion of the subject of interest (28);
a method of controlling an energy depositing therapy system (10) by a magnetic resonance rheology system; and
an application software module (50) provided to carry out one of the disclosed methods or combinations thereof.

12 Claims, 6 Drawing Sheets

(51) Int. Cl.
| | | |
|---|---|---|
| *G01R 33/48* | (2006.01) | |
| *A61N 7/02* | (2006.01) | |
| *A61B 90/00* | (2016.01) | |
| *A61B 5/055* | (2006.01) | |
| A61B 18/00 | (2006.01) | |
| G01R 33/563 | (2006.01) | |
| A61N 5/10 | (2006.01) | |
| A61N 7/00 | (2006.01) | |

(52) U.S. Cl.
CPC .......... *A61B 18/1815* (2013.01); *A61B 90/37* (2016.02); *A61N 7/02* (2013.01); *G01R 33/4808* (2013.01); A61B 2018/0019 (2013.01); A61B 2018/00577 (2013.01); A61B 2018/00642 (2013.01); A61B 2018/00898 (2013.01); A61B 2018/00904 (2013.01); A61B 2090/374 (2016.02); A61N 2005/1055 (2013.01); A61N 2007/0078 (2013.01); G01R 33/56358 (2013.01)

(56) References Cited

U.S. PATENT DOCUMENTS

| | | | |
|---|---|---|---|
| 6,506,171 B1* | 1/2003 | Vitek | A61H 23/0245 600/439 |
| 2004/0170086 A1* | 9/2004 | Mayer | H04R 1/083 367/178 |
| 2005/0080333 A1* | 4/2005 | Piron | A61B 8/0825 600/417 |
| 2006/0089625 A1* | 4/2006 | Voegele | A61B 17/3421 606/1 |
| 2006/0206105 A1* | 9/2006 | Chopra | A61B 5/055 606/27 |
| 2008/0255444 A1* | 10/2008 | Li | A61B 5/055 600/411 |
| 2008/0298660 A1* | 12/2008 | Yamagata | A61B 6/032 382/131 |
| 2009/0105588 A1* | 4/2009 | Emelianov | A61B 5/4869 600/438 |
| 2009/0123384 A1* | 5/2009 | Wald | G01R 33/5601 424/9.32 |
| 2010/0010595 A1* | 1/2010 | Bruggers | A61N 7/02 607/96 |
| 2010/0026298 A1* | 2/2010 | Wald | G01R 33/5616 324/309 |
| 2010/0125192 A1* | 5/2010 | Chopra | A61N 7/02 600/411 |
| 2010/0174189 A1* | 7/2010 | Abraham | A61B 5/076 600/439 |
| 2010/0262989 A1 | 10/2010 | Lanfermann | |
| 2011/0131278 A1 | 6/2011 | Nieh | |
| 2011/0160566 A1* | 6/2011 | Petropoulos | A61N 5/1049 600/411 |
| 2011/0178386 A1* | 7/2011 | Grissom | G01R 33/4804 600/410 |
| 2011/0208055 A1* | 8/2011 | Dalal | A61N 7/02 600/439 |
| 2011/0306870 A1* | 12/2011 | Kuhn | A61B 5/0515 600/411 |
| 2011/0313278 A1 | 12/2011 | Kiraly | |
| 2012/0029353 A1* | 2/2012 | Slayton | A61N 7/02 600/439 |
| 2012/0035464 A1* | 2/2012 | Raju | A61N 7/02 600/411 |
| 2012/0083686 A1 | 4/2012 | Virta et al. | |
| 2012/0253176 A1* | 10/2012 | Dumoulin | A61N 7/02 600/411 |
| 2012/0259201 A1 | 10/2012 | Chen | |
| 2013/0158387 A1* | 6/2013 | Tanttu | G01R 33/4804 600/411 |
| 2013/0197357 A1* | 8/2013 | Green | A61B 8/0841 600/424 |
| 2013/0217950 A1* | 8/2013 | Partanen | G01R 33/4814 600/1 |
| 2014/0058387 A1* | 2/2014 | Kruecker | A61B 18/148 606/41 |
| 2014/0073907 A1* | 3/2014 | Kumar | A61B 10/00 600/414 |
| 2014/0257262 A1* | 9/2014 | Carpentier | A61N 7/02 606/28 |
| 2014/0316269 A1* | 10/2014 | Zhang | A61B 8/4494 600/439 |
| 2014/0343404 A1* | 11/2014 | Razzaque | A61B 8/0841 600/424 |
| 2014/0366878 A1* | 12/2014 | Baron | G16H 40/63 128/204.23 |
| 2015/0005756 A1* | 1/2015 | Tillander | A61N 7/02 606/27 |
| 2016/0008074 A1* | 1/2016 | Glossop | A61B 19/20 606/130 |
| 2016/0008634 A1* | 1/2016 | Payne | A61B 8/4227 600/411 |

OTHER PUBLICATIONS

Sinkus et al "MR Elastography of Breast Lesions: Understanding the Solid/Liquid Duality Can Improve the Specificity of Contrast-Enhanced MR Mammography" Magnetic Resonance in Medicine, 58 p. 1135-1144 (2007).

Rossman et al "Piezoelectric Bending Elements for use as Motion Actuators in MR Elastography" Proc. Intl. Soc. Mag. Reson. 11 p. 1075 (2003).

Sinkus et al, "High-Resolution Tensor MR Elastography for Breast Tumor Detection" Phys.Med. Biol. 45 p. 1649-1664 (2000).

\* cited by examiner

REAL TIME ENERGY DEPOSITING THERAPY SYSTEM CONTROLLED BY MAGNETIC RESONANCE RHEOLOGY

CROSS REFERENCE TO RELATED APPLICATIONS

This application is a U.S. national phase application of International Application No. PCT/EP2014/056288, filed on Mar. 28, 2014, which claims the benefit of EP Application Serial No. 13162495.9 filed on Apr. 5, 2013 and is incorporated herein by reference.

FIELD OF THE INVENTION

The invention pertains to an energy depositing therapy system comprising a magnetic resonance imaging system, and a method of controlling an energy depositing therapy system by a magnetic resonance rheology system.

BACKGROUND OF THE INVENTION

In the art of magnetic resonance imaging, it is known to characterize the mechanical properties of human or animal tissue by magnetic resonance rheology (cf., for instance, to Muthipillai R. et al., *Magnetic resonance imaging of acoustic strain waves*, Proc. Soc. Magn. Reson. Nice, 1:189, 1995). In magnetic resonance rheology, tissue is driven to mechanically oscillate during magnetic resonance imaging, leading to effects which cause an imaging contrast. Low-frequency mechanical waves are coupled into the tissue and are visualized via a magnetic resonance sequence which is phase-locked to the mechanical excitation. Conventional palpation has turned into the assessment of an objective absolute physical quantity, whose diagnostic value can be quantified. This information can be used, for instance, to distinguish healthy from malign tissue.

U.S. patent application 2011/0131278 mentions to employ magnetic resonance elastography to derive a temperature distribution caused by applying high-intensity focused ultrasound (HIFU). Therein, it is suggested to correlate magnetic resonance elastography data to a temperature-dependent viscosity to retrospectively monitor the thermal effect of the HIFU application as a replacement for proton resonance frequency shift measurements.

SUMMARY OF THE INVENTION

It is therefore an object of the invention to provide an energy depositing therapy system with an improved visualization of and improved specificity for malign tissue.

In one aspect of the present invention, the object is achieved by an energy depositing therapy system, comprising:

an energy depositing unit provided for locally depositing energy into a therapy zone of a subject of interest for therapy purposes;

a transducer unit having at least one mechanical transducer that can be mechanically coupled to the subject of interest and that is provided for applying mechanical oscillations to at least a portion of the subject of interest;

a magnetic resonance imaging system provided for acquiring magnetic resonance imaging data from at least the portion of a subject of interest, comprising:

a magnetic resonance scanner; and an image processing unit configured to image the mechanical oscillations in at least the portion of the subject of interest by processing the acquired magnetic resonance imaging data of the portion of the subject of interest;

a control unit that is connectable to the energy depositing unit, the transducer unit and the magnetic resonance scanner, wherein the control unit is configured to control the depositing of energy in dependence of the processed magnetic resonance imaging data of the portion of the subject of interest.

The phrase "therapy zone", as used in this application, shall be understood particularly as a zone of tissue of the subject of interest which (a) has been identified to require treatment in form of depositing energy, and (b) has to be protected from excessive energy deposition. Usually, malign tissue is surrounded by healthy, functional tissue which needs to survive the treatment.

By that, a substantial rise in specificity, for instance for cancer diagnosis, and an improved visualization for distinguishing malign tissue from healthy tissue can be achieved in preparation of the depositing of energy. This improved differentiation also supports a precise and safe energy depositing into the therapy zone of the subject of interest.

The processing of the acquired magnetic resonance imaging data of the portion of the subject of interest may comprise a magnetic resonance imaging technique based on phase-contrast. The acquiring of the magnetic resonance imaging data may be phase-locked with the applied mechanical oscillations for noise reduction and improvement of a signal-to-noise ratio, as is known in the art.

The control unit may be connectable to the energy depositing unit, the transducer unit and the magnetic resonance scanner by wire connections or by wireless connections or by a combination of both.

A number of different mechanical transducers for applying the mechanical oscillations to the tissue have been proposed, such as electromagnetic designs, which make use of the main magnetic field $B_0$ inside the MR scanner. Further, piezo-driven transducers or pneumatic designs were proposed for clinical application. In general, any mechanical transducer that appears to be suitable to the one skilled in the art may be employed.

In another embodiment, the control unit is configured to disable energy depositing by the energy depositing unit if a target zone is distinct from the therapy zone. The phrase "target zone", as used in this application, shall be understood particularly as the tissue volume within the subject of interest that the energy depositing unit would deposit 95% of the energy to in a moment of activation of the energy depositing unit. By that, a potentially unsafe enabling of the energy depositing into the target zone which is distinct from the therapy zone of the subject of interest can be prevented.

In yet another embodiment, the control unit is configured to enable energy depositing by the energy depositing unit only if the target zone at least partially overlaps with the therapy zone. By this, and based on the improved differentiation, a precise and safe energy depositing into the therapy zone of the subject of interest can be achieved.

In a preferred embodiment, the energy depositing therapy system comprises an ablation unit configured for ablating tissue from the subject of interest. By this, a safe and precise excision of malign tissue from the subject of interest can be achieved. The ablation unit may be controlled manually by a human user, or it may be controlled by a non-human user, such as a robot.

In another preferred embodiment, the energy depositing unit comprises at least one out of a high-intensity focused ultrasound (HIFU) device, a microwave ablation unit, a shockwave generation device, a hyperthermia device and a radiation therapy device. This shall particularly also encompass a combination of two or more of the mentioned devices. By that, the advantages of the invention can be used in a wide scope of applications.

In some embodiments, the transducer unit comprises at least one open access for an interventional device. By that, wide options of access for the interventional device can be provided with little interference by the mechanical transducer.

In yet another embodiment, the transducer unit comprises a honeycomb structure, wherein the at least one mechanical transducer resides in a first honeycomb of the honeycomb structure, and the at least one open access is provided in a second honeycomb of the honeycomb structure adjacent to the first honeycomb. By this, options of access for the interventional device can be ready provided in combination with a rigid and well-defined relative arrangement of the mechanical transducer and the interventional device. The honeycomb structure preferably has a mass density about $1/7$ (±20%) of the same solid material as which the honeycomb structure is made of. The honeycomb structure provides sufficient mechanical stiffness to be able to stable support the transducer unit when in operation. In this way a stable and well controlled field of mechanical shear waves can be generated in the patient's tissue. Because of its open structure and lower mass density the honeycomb structure has low reflectivity for energy depositing radiation from the energy depositing unit. Notably when the energy deposition is done by ways of high-intensity focused ultrasound, the relative orientations of the HIFU device and the transducer unit are not subject to restrictions. Notably, there is no need to avoid reflections by the honeycomb structure of HIFU radiation. Good results are achieved with a honeycomb structure having a mass density of 21-192 kgm$^3$. The piston and the housing of the transducer unit may be made of polycarbonate having a mass density in the range of 1200-1220 kgm$^3$.

In still another embodiment, the transducer unit has at least two mechanical transducers that are integrated with the energy depositing unit in a single housing. In a suitable arrangement of the two mechanical transducers, an energy depositing therapy system can be provided that is especially useful for therapy of mammae.

In another aspect of the present invention, the object is achieved by a method of controlling an energy depositing therapy system by a magnetic resonance rheology system, the energy depositing therapy system comprising an energy depositing unit provided for locally depositing energy into a therapy zone of a subject of interest for therapy purposes;

a transducer unit having at least one mechanical transducer;

a magnetic resonance imaging system comprising a magnetic resonance scanner and an image processing unit;
the method comprising following steps:

mechanically couple the mechanical transducer to the subject of interest;

activate the mechanical transducer for applying mechanical oscillations at least to a portion of the subject of interest;

acquire magnetic resonance imaging data from the portion of the subject of interest;

image the mechanical oscillations in the portion of the subject of interest by processing the acquired magnetic resonance imaging data;

identify a target zone of the energy depositing unit within the processed magnetic resonance imaging data; and omitting energy depositing by the energy depositing unit if the target zone is distinct from the therapy zone.

By applying this method, a substantial rise in specificity, for instance for cancer diagnosis, and an improved visualization for distinguishing malign tissue from healthy tissue can be achieved in preparation of the depositing of energy. Moreover, the method prevents a potentially unsafe enabling of the energy depositing into the target zone which is distinct from the therapy zone of the subject of interest.

In yet another aspect of the present invention, the object is achieved by a method of controlling an energy depositing therapy system by a magnetic resonance rheology system, the energy depositing therapy system comprising an energy depositing unit provided for locally depositing energy into a therapy zone of a subject of interest for therapy purposes;

a transducer unit having at least one mechanical transducer;

a magnetic resonance imaging system comprising a magnetic resonance scanner and an image processing unit;
the method comprising following steps:

mechanically couple the mechanical transducer to the subject of interest;

activate mechanical transducer for generating mechanical oscillations at least within a portion of the subject of interest;

acquire magnetic resonance imaging data from the portion of the subject of interest;

image the mechanical oscillations in the portion of the subject of interest by processing the acquired magnetic resonance imaging data;

identify a target zone of the energy depositing unit in the processed magnetic resonance imaging data; and deposit energy by the energy depositing unit only if the target zone at least partially overlaps with the therapy zone.

By applying this method, a substantial rise in specificity, for instance for cancer diagnosis, and an improved visualization for distinguishing malign tissue from healthy tissue can be achieved in preparation of the depositing of energy. The improved differentiation also supports a precise and safe energy depositing into the therapy zone of the subject of interest.

In another preferred embodiment of the method, the mechanical transducer is deactivated during the depositing of energy by the energy depositing unit. By that, any interference between the energy depositing unit and the transducer unit can be avoided while the advantage of the method is still maintained.

In another aspect of the invention, the object is achieved by an application software module provided to carry out one of the disclosed methods or combinations thereof, wherein the method is converted into a program code that is implementable in and executable by a control unit that is connectable to the energy depositing unit, the transducer unit and the magnetic resonance imaging system, and that is provided to control an energy depositing therapy system by carrying out the method.

BRIEF DESCRIPTION OF THE DRAWINGS

These and other aspects of the invention will be apparent from and elucidated with reference to the embodiments described hereinafter. Such embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
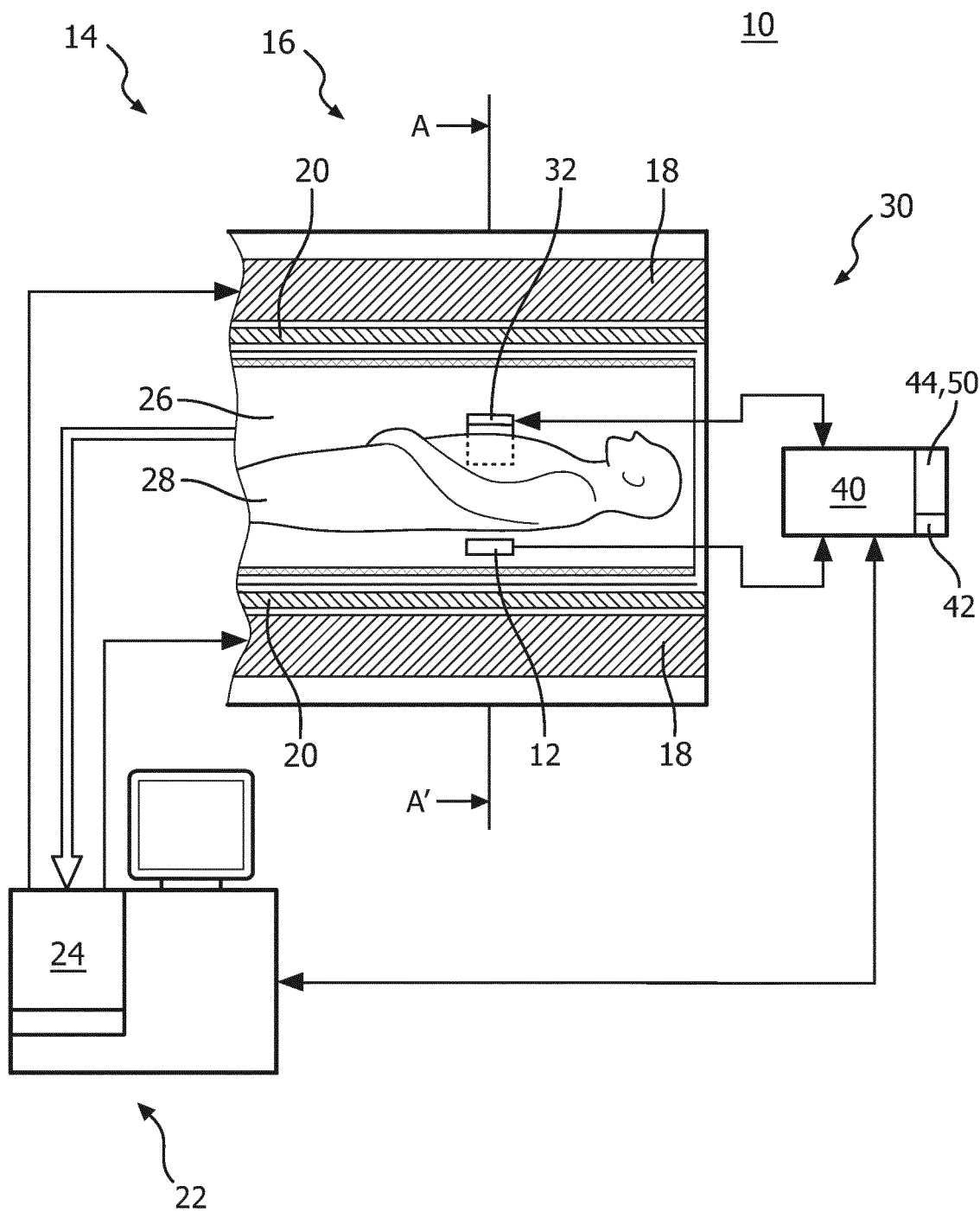
FIG. 1 shows a schematic partial illustration of an energy depositing therapy system in accordance with the invention.

FIG. 1 shows a schematic partial illustration of an energy depositing therapy system 10 in accordance with the invention.

The energy depositing therapy system 10 comprises a magnetic resonance imaging system 14 provided for acquiring magnetic resonance imaging data from at least a portion of a subject of interest 28, usually a patient. The magnetic resonance imaging system 14 includes a magnetic resonance scanner 16 comprising a main magnet 18 with a center bore that defines an examination space 26 for the subject of interest 28 to be positioned within. A patient table has been omitted in FIG. 1 for reasons of clarity. The main magnet 18 is provided for generating a substantially static magnetic field in the examination space 26, wherein the substantially static magnetic field is directed substantially parallel to a center axis of the examination space 26. Further, the magnetic resonance imaging system 14 comprises a magnetic gradient coil system 20 for generating gradient magnetic fields superimposed to the static magnetic field. The magnetic gradient coil system 20 is concentrically arranged within the bore of the main magnet 18, as is well known in the art.

The magnetic resonance imaging system 14 further includes a magnetic resonance imaging system control unit 22 with a monitoring unit to control functions of the magnetic resonance scanner 16, as is commonly known in the art, and an image processing unit 24 provided for processing magnetic resonance signals acquired from the subject of interest 28.

Figure 3:
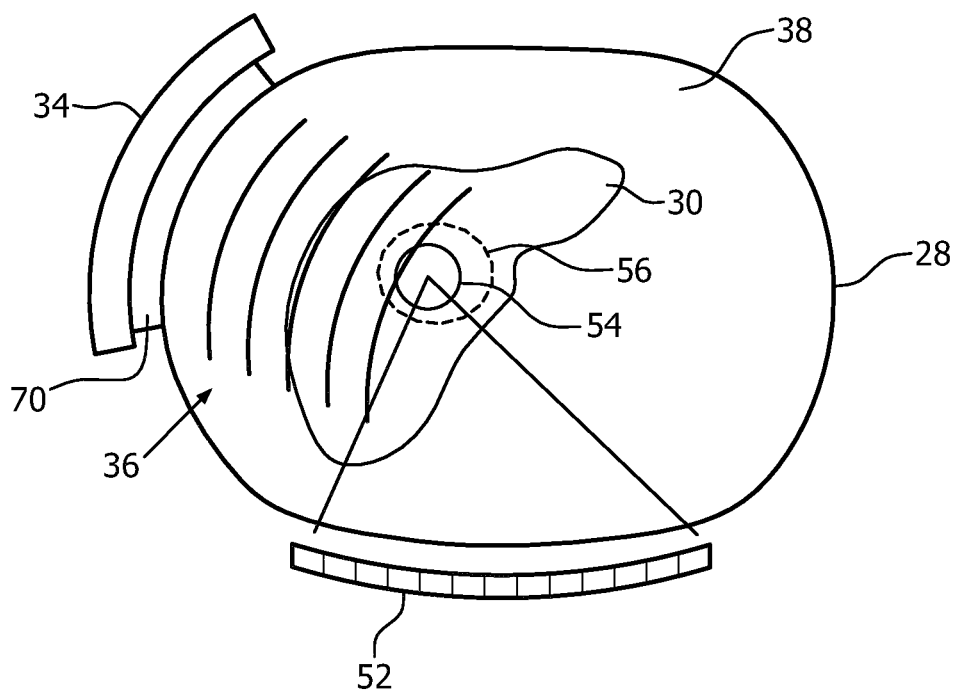
FIG. 3 is a partial cross-sectional view of the energy depositing unit pursuant to FIG. 1 onto the plane A-A', FIG. 4 schematically illustrates an alternative embodiment of an energy depositing unit in accordance with the invention in the same view as FIG. 3.

The energy depositing therapy system 10 further comprises an energy depositing unit 12 provided for locally depositing energy into a therapy zone 56 of the subject of interest 28 for therapy purposes (FIG. 3). In the embodiment of FIG. 1, the energy depositing unit 12 comprises an ablation unit designed as a high-intensity focused ultrasound (HIFU) array 52 and configured for ablating tissue 38 from the subject of interest 28 (FIG. 3). The one skilled in the art may note that such a HIFU unit may also be utilized as a hyperthermia device, depositing energy in the target zone in order to activate tissue for improved response to e.g. chemotherapy. An energy depositing unit target zone 54 is controlled by a human user or by a non-human user, such as a robot. The target zone 54 is defined as the tissue volume within the subject of interest 28 in which 95% of the energy was deposited if the energy depositing unit 12 was activated.

Furthermore, the energy depositing therapy system 10 comprises a transducer unit 32 (FIG. 2) having a plurality of mechanical transducers 34 of the electromechanical type which are arranged to form an array (FIG. 3), and that can be simultaneously operated by a driving amplifier (not shown). In an operational state of the energy depositing therapy system 10, the mechanical transducers 34 are mechanically coupled to the subject of interest 28 and are provided for applying mechanical oscillations at a frequency of 200 Hz to at least the portion of the subject of interest 28. By applying mechanical oscillations to the portion of the subject of interest 28, the mechanical transducers 34 generate shear waves 36 propagating within the tissue 38 of the subject of interest 28. The frequency of the applied mechanical oscillations may be different than 200 Hz and may be selected out of a range between 10 Hz and 1100 Hz, as is known in the art of magnet resonance rheology.

Regarding timing, the acquiring of the magnetic resonance imaging data is phase-locked with the applied mechanical oscillations for noise reduction and improvement of a signal-to-noise ratio. The image processing unit 24 (FIG. 1) is, amongst other things, configured to image the mechanical oscillations in the portion of the subject of interest 28 by processing the acquired magnetic resonance imaging data of the portion of the subject of interest 28 by applying a magnetic resonance imaging technique based on phase-contrast. By that, the magnetic resonance images show the propagating shear waves 36, and different types of tissue 38 can be clearly distinguished by the different ways in which the shear waves 36 propagate within the tissue 38.

Figure 2:
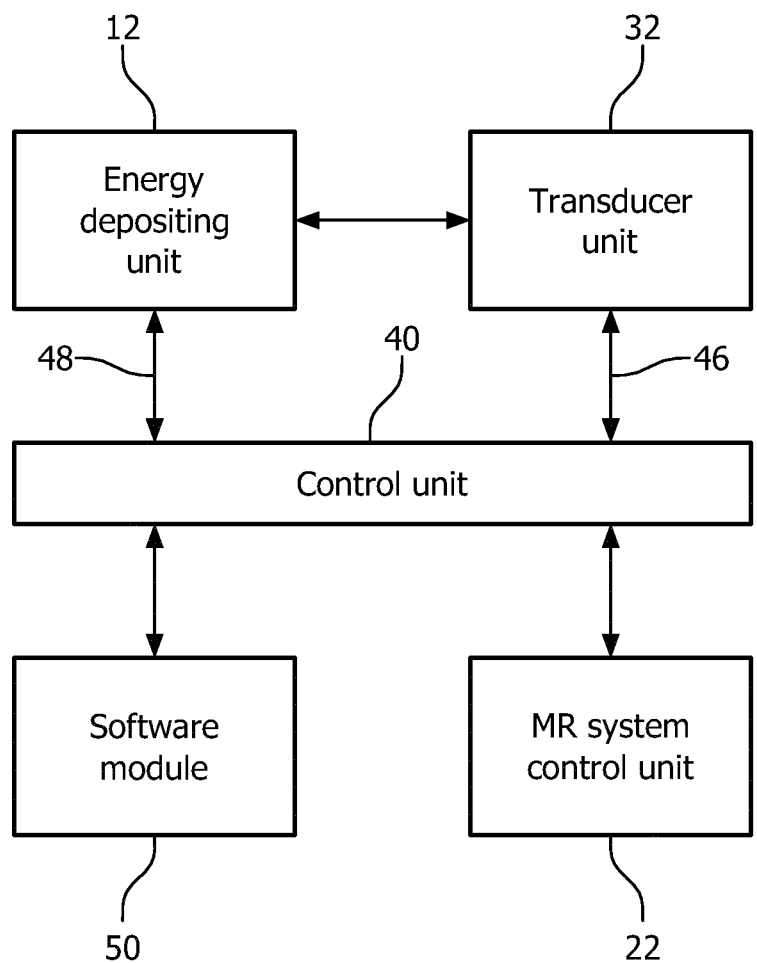
FIG. 2 shows a schematic diagram of an interconnection of components of the energy depositing therapy system pursuant to FIG. 1.

The energy depositing unit 12, the transducer unit 32 and the magnetic resonance scanner 16 are interconnected by wire connections via a control unit 40 of the energy depositing therapy system 10, as is schematically illustrated in FIGS. 1 and 2.

For operation of the energy depositing therapy system 10, the transducer unit 32 can be controlled by a first hardware interface 46 of the control unit 40, which is located close to the magnetic resonance scanner 16, and the energy depositing unit 12 can be triggered by a second hardware interface 48 of the control unit 40. In dependence of the processed magnetic resonance imaging data of the subject of interest 28, the control unit 40 is configured to control the depositing of energy by the energy depositing unit 12, as will be described in detail further below.

In preparation of an operation of the energy depositing therapy system 10, it shall be understood that the subject of interest 28, the patient, is positioned within the examination space 26 of the magnetic resonance scanner 16, and that the transducer unit 32 is in a ready-to-operate state, with the mechanical transducers 34 coupled to the subject of interest 28. A water-based gel 70 is usually provided between the mechanical transducers 34 and a surface of the subject of interest 28 for efficiently transmitting any applied mechanical oscillations. The energy depositing unit 12 is understood to be in a ready-to-operate state, and the magnetic resonance imaging system 14 is operable and ready for acquiring magnetic resonance signals from the subject of interest 28. Also, the therapy zone 56 within the subject of interest 28 has been identified for therapy purposes prior to the treatment. In FIG. 3, the therapy zone 56 is indicated by a dotted line within an organ 30 (liver) of the subject of interest 28.

In a next step, the control unit 40 activates the mechanical transducers 34 via the transducer unit 32 for applying mechanical oscillations to the portion of the subject of interest 28, generating the shear waves 36 propagating within the tissue 38 of the subject of interest 28. While the mechanical oscillations are being applied, the control unit 40 activates the magnetic resonance imaging system 14 via the magnetic resonance system control unit 22 to acquire magnetic resonance imaging data from the portion of the subject of interest 28. Then, the image processing unit 24 processes the acquired magnetic resonance imaging data by applying a magnetic resonance imaging technique based on phase-contrast to image the mechanical oscillations in the portion of the subject of interest 28.

By requesting data from the energy depositing unit 12 via the second hardware interface 48, the control unit 40 identifies the target zone 54 of the energy depositing unit 12 within the processed magnetic resonance imaging data.

If the target zone 54 is distinct from the therapy zone 56, the control unit 40 disables the energy depositing function of the energy depositing unit 12 so that the depositing of energy is omitted. By that, a potentially unsafe enabling of the energy depositing into the target zone 54 is prevented, irrespective of whether a location of the energy depositing unit target zone 54 is controlled by a human user or by a non-human user, such as a robot.

If the target zone 54 at least partially overlaps with the therapy zone 56 (in the embodiment of FIG. 3, the target zone 54 completely lies within the therapy zone 56), the control unit 40 enables the energy depositing function of the energy depositing unit 12 so that energy will be deposited if the human user or the non-human user, such as a robot, releases the energy depositing function of the energy depositing unit 12.

To prevent any interference between the mechanical transducers 34 and the energy depositing unit 12, the control unit 40 deactivates the mechanical transducers 34 via the first hardware interface 46 during the depositing of energy by the energy depositing unit 12.

In order to carry out the method steps disclosed above, the control unit 40 is equipped with an application software module 50 comprising the method steps converted into a program code that is implemented in a control unit memory 44 and executable by a control unit processor 42 (FIG. 1).

The following description contains several alternative embodiments of the invention. The individual alternative embodiments are described with reference to a particular figure or group of figures and are identified by a prefix number of the particular embodiment. Features whose function is the same or basically the same in all embodiments are identified by reference numbers made up of the prefix number of the embodiment to which it relates, followed by the number of the feature. If a feature of an embodiment is not described in the corresponding figure depiction, or a reference number mentioned in a figure depiction is not shown in the figure itself, reference is herewith made to the description of a preceding embodiment.

Figure 4:
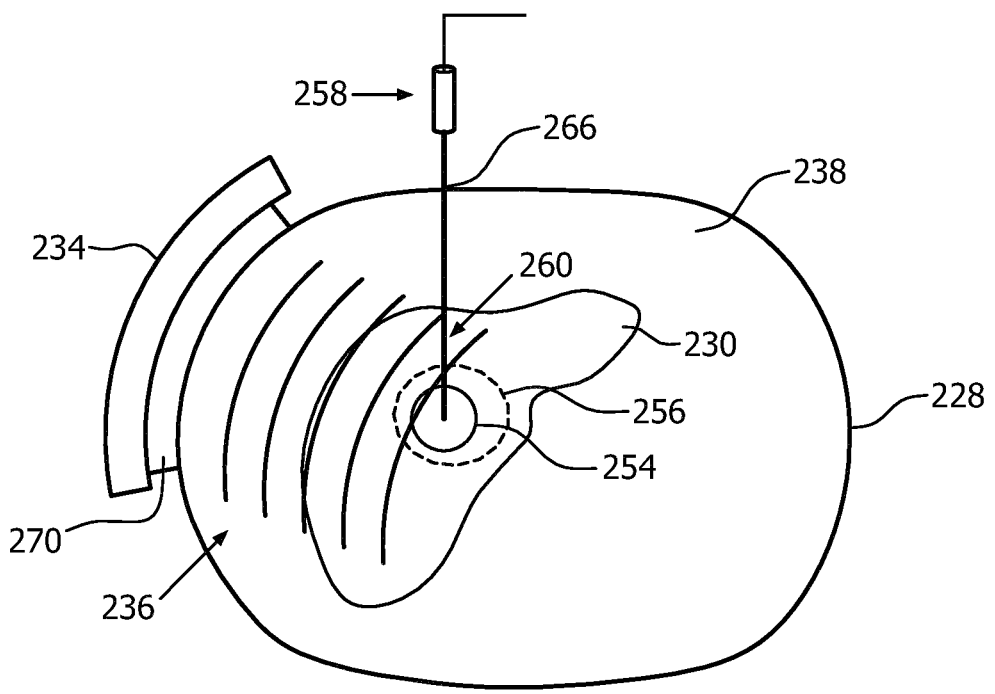

FIG. 4 schematically and partially illustrates an alternative embodiment of an energy depositing therapy system 210 in accordance with the invention in the same view as FIG. 3. In contrast to the embodiment pursuant to FIGS. 1 and 3, the energy depositing therapy system 210 includes an energy depositing unit 212 that comprises a microwave ablation unit 258 including a microwave generation device (not shown). The microwave ablation unit 258 is combined with a biopsy device 260 for sampling tissue 238 of a subject of interest 228, using an identical access 266 to a therapy zone 256.

Figure 5:
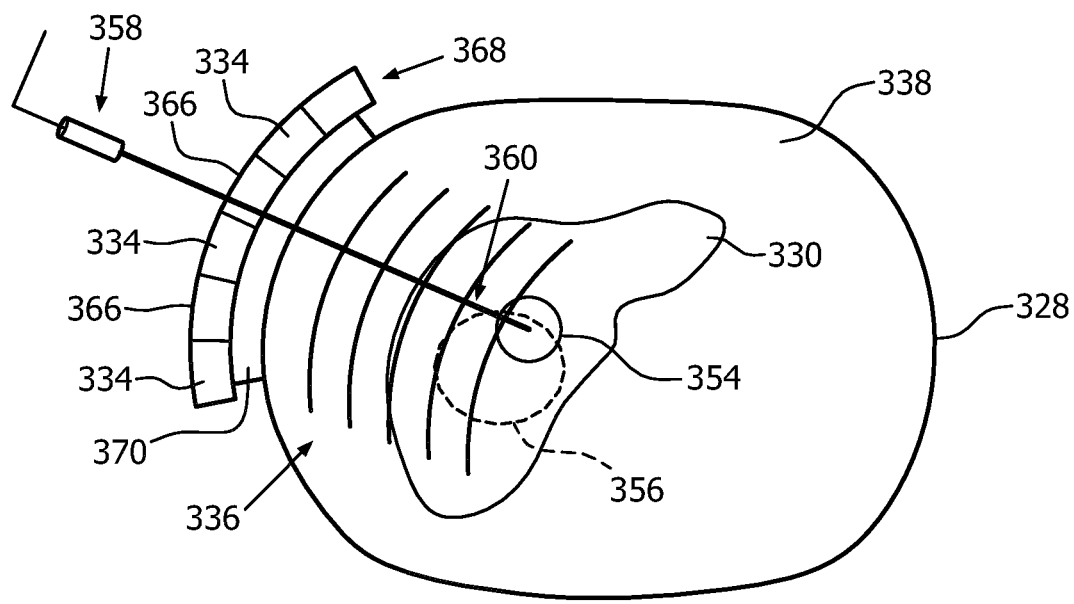
FIG. 5 is a schematic illustration of another alternative embodiment of an energy depositing unit in accordance with the invention in the same view as FIG. 3.

FIG. 5 schematically and partially illustrates another alternative embodiment of an energy depositing therapy system 310 in accordance with the invention in the same view as FIG. 3. In contrast to the embodiment disclosed in FIG. 4, a transducer unit 332 of the energy depositing therapy system 310 comprises a number of open accesses 366 for an interventional device. To this end, the transducer unit 332 comprises a honeycomb structure 368 with a number of honeycombs, in which a mechanical transducer 334 is arranged in every other honeycomb. Honeycombs between the mechanical transducers 334, adjacent to the honeycombs with the mechanical transducers, each provide an open access 366 for an interventional device designed as a combination of a microwave ablation unit 358 and a biopsy device 360. (See also, FIG. 8, and its description below.)

Figure 6:
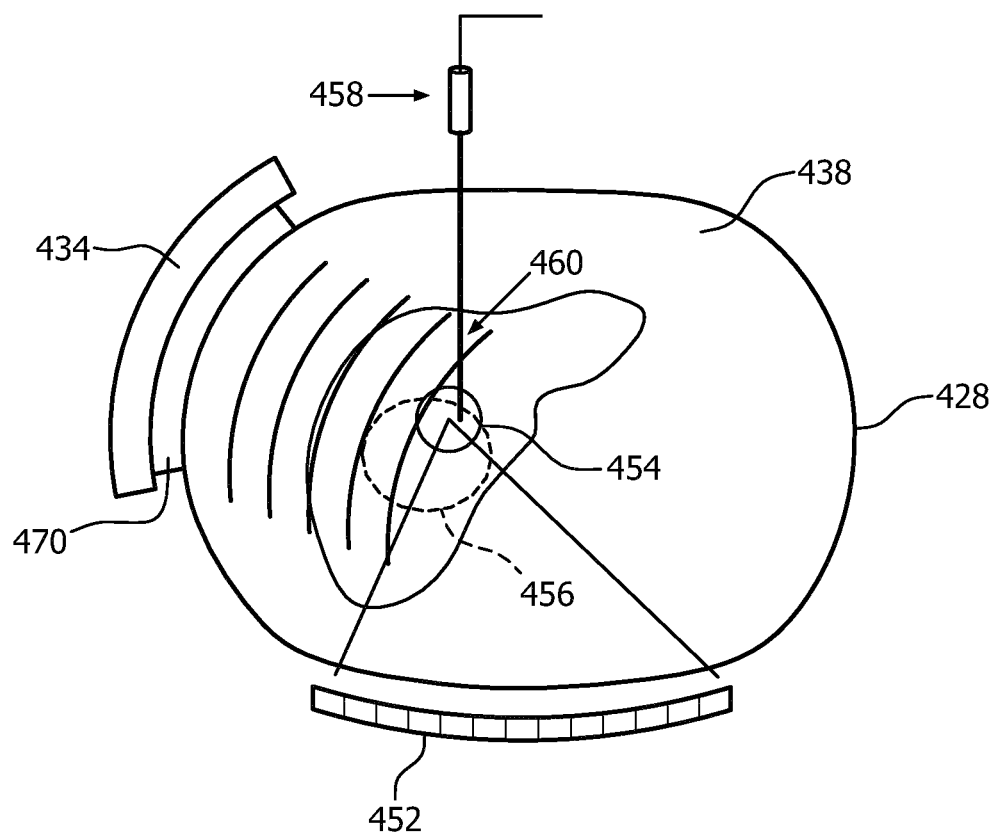
FIG. 6 is a schematic illustration of yet another alternative embodiment of an energy depositing unit in accordance with the invention in the same view as FIG. 3, and FIG. 7 schematically illustrates another alternative embodiment of an energy depositing unit in accordance with the invention in the same view as FIG. 3.

FIG. 6 schematically illustrates yet another alternative embodiment of an energy depositing therapy system 410 which is similar to the embodiment shown in FIG. 3. In contrast to the embodiment shown in FIG. 3, the energy depositing therapy system 410 comprises an energy depositing unit 412 which, besides the high-intensity focused ultrasound device 452, additionally comprises a combination of a microwave ablation unit 458 having a microwave generation device (not shown), and a biopsy device 460.

Figure 7:
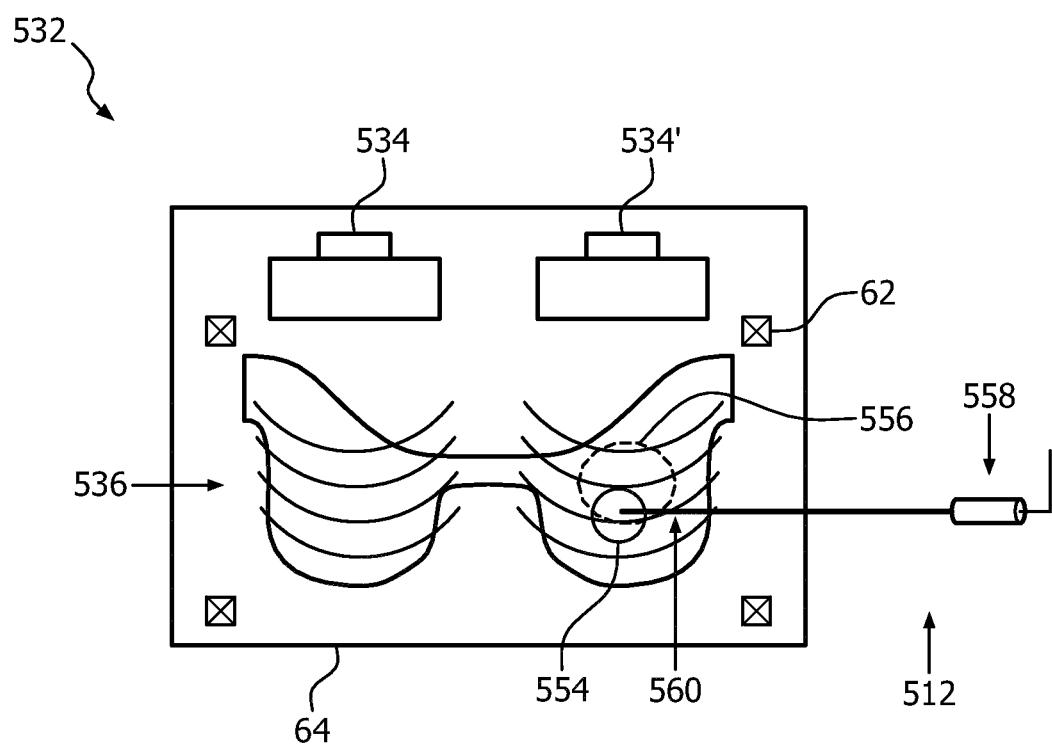

FIG. 7 schematically illustrates another alternative embodiment of an energy depositing therapy system 510, comprising a transducer unit 532 having two mechanical transducers 534, 534' and an energy depositing unit 512 that comprises a combination of a microwave ablation unit 558 having a microwave generation device (not shown), and a biopsy device 560. The energy depositing therapy system 510 comprises a magnetic resonance imaging system 514 having a radio frequency antenna 62 provided for excitation and reception of magnetic resonance signals from mammae of a subject of interest 528. Radio frequency antennae 62 of this kind are well-known in the art and shall therefore not described further herein. The radio frequency antenna 62, the two mechanical transducers 534, 534' and the energy depositing unit 512 are integrated in a single housing 64, providing a solution that is especially configured for an energy depositing therapy of mammae.

Figure 8:
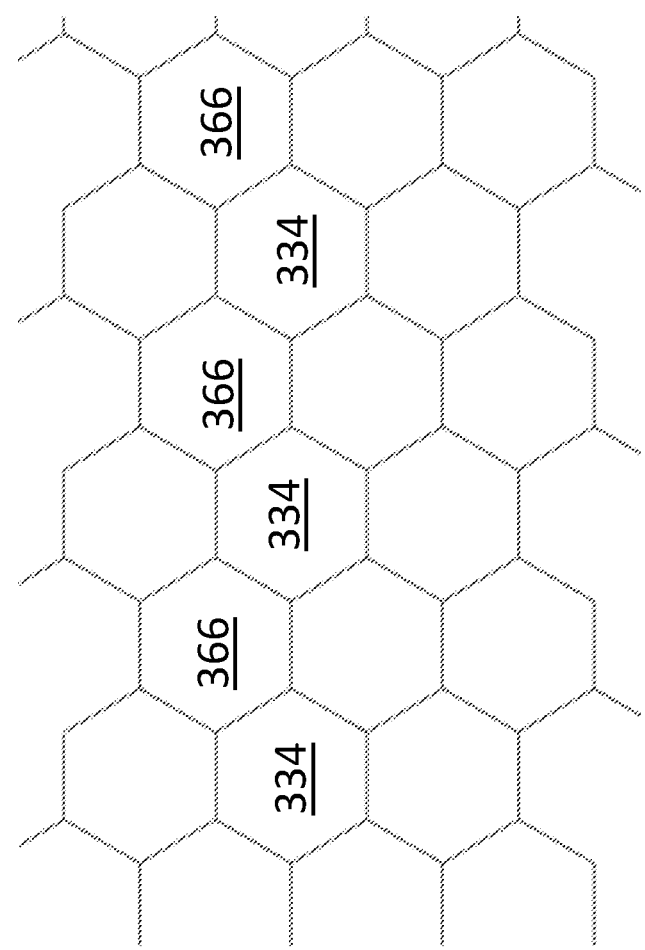
FIG. 8 is a partial top view of a portion of the transducer unit shown in FIG. 3.

FIG. 8 is a top view of a portion of the transducer unit 332 comprising a honeycomb structure in accordance with a representative embodiment. As noted above in connection with the embodiment of FIG. 3, mechanical transducers 334 are arranged in every other honeycomb, referred to as first honeycombs. Second honeycombs between the mechanical transducers 334, adjacent to the first honeycombs with the mechanical transducers, each provide an open access 366 for an interventional device designed as a combination of a microwave ablation unit 358 and a biopsy device 360. In this way, the transducer unit comprises mechanical transducers 334 disposed in alternating first honeycombs, and open accesses in alternating second honeycombs.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST

| 10 | energy depositing therapy system |
|---|---|
| 12 | energy depositing unit |
| 14 | magnetic resonance imaging system |
| 16 | magnetic resonance scanner |
| 18 | main magnet |
| 20 | magnetic gradient coil system |
| 22 | magnetic resonance imaging system control unit |
| 24 | image processing unit |
| 26 | examination space |
| 28 | subject of interest |
| 30 | organ |
| 32 | transducer unit |
| 34 | mechanical transducer |
| 36 | shear wave |
| 38 | tissue |
| 40 | control unit |
| 42 | control unit processor |
| 44 | control unit memory |
| 46 | first hardware interface |
| 48 | second hardware interface |
| 50 | application software module |
| 52 | high-intensity focused ultrasound array |
| 54 | target zone |
| 56 | therapy zone |
| 58 | microwave ablation unit |
| 60 | biopsy device |
| 62 | radio frequency antenna |
| 64 | housing |
| 66 | open access |
| 68 | honeycomb structure |
| 70 | water-based gel |

The invention claimed is:

1. An energy depositing therapy system, comprising:
an energy depositing unit provided for locally depositing energy into a therapy zone of a subject of interest for therapy purposes;
a transducer unit comprising a honeycomb structure having mechanical transducers disposed in alternating first honeycombs, and open accesses in alternating second honeycombs, the transducer unit being configured to be mechanically coupled to the subject of interest and that is provided for applying mechanical oscillations to at least a portion of the subject of interest, wherein the open accesses are configured to receive an interventional device; and
a magnetic resonance imaging system provided for acquiring magnetic resonance imaging data from at least the portion of the subject of interest, comprising:
a magnetic resonance scanner;
an image processing unit configured to image the mechanical oscillations in at least the portion of the subject of interest by processing the acquired magnetic resonance imaging data of the portion of the subject of interest; and
a control unit that is connectable to the energy depositing unit, the transducer unit and the magnetic resonance scanner, wherein the control unit is configured to control the depositing of energy in dependence of the processed magnetic resonance imaging data of the portion of the subject of interest.

2. The energy depositing therapy system of claim 1, wherein the control unit is configured to disable energy depositing by the energy depositing unit when a target zone is distinct from the therapy zone.

3. The energy depositing therapy system of claim 1, wherein the control unit is configured to enable energy depositing by the energy depositing unit only when a target zone at least partially overlaps with the therapy zone.

4. The energy depositing therapy system of claim 1, wherein the energy depositing unit comprises an ablation unit configured for ablating tissue from the subject of interest.

5. The energy depositing therapy system of claim 1, wherein the energy depositing unit comprises at least one out of a high-intensity focused ultrasound device, a microwave ablation unit, a shockwave generation device, a hyperthermia device and a radiation therapy device.

6. The energy depositing therapy system of claim 1, wherein the transducer unit has at least two mechanical transducers that are integrated with the energy depositing unit in a single housing.

7. An energy depositing therapy system, comprising:
an energy depositing unit provided for locally depositing energy into a therapy zone of a subject of interest for therapy purposes;
a transducer unit comprising a honeycomb structure having mechanical transducers disposed in first honeycombs, and an open access in a second honeycomb, the transducer unit being configured to be mechanically coupled to the subject of interest and that is provided for applying mechanical oscillations to at least a portion of the subject of interest, wherein the one open access is configured to receive an interventional device;
a magnetic resonance imaging system provided for acquiring magnetic resonance imaging data from at least the portion of a subject of interest, comprising:
a magnetic resonance scanner;
an image processing unit configured to image the mechanical oscillations in at least the portion of the subject of interest by processing the acquired magnetic resonance imaging data of the portion of the subject of interest; and
a control unit that is connectable to the energy depositing unit, the transducer unit and the magnetic resonance scanner, wherein the control unit is configured to control the depositing of energy in dependence of the processed magnetic resonance imaging data of the portion of the subject of interest.

8. The energy depositing therapy system of claim 7, wherein the control unit is configured to disable energy depositing by the energy depositing unit when a target zone is distinct from the therapy zone.

9. The energy depositing therapy system of claim 7, wherein the control unit is configured to enable energy depositing by the energy depositing unit only when a target zone at least partially overlaps with the therapy zone.

10. The energy depositing therapy system of claim 7, wherein the energy depositing unit comprises an ablation unit configured for ablating tissue from the subject of interest.

11. The energy depositing therapy system of claim 7, wherein the energy depositing unit comprises at least one out of a high-intensity focused ultrasound device, a microwave ablation unit, a shockwave generation device, a hyperthermia device and a radiation therapy device.

12. The energy depositing therapy system of claim 7, wherein the transducer unit has at least two mechanical transducers that are integrated with the energy depositing unit in a single housing.

* * * * *